United States Patent [19]

Miremadi et al.

[11] Patent Number: 5,245,124

[45] Date of Patent: Sep. 14, 1993

[54] ETHYLENE FROM METHANE AND CATALYSTS THEREFOR

[75] Inventors: Bijan K. Miremadi, Coquitlam; Stanley R. Morrison, Burnaby; Konrad Colbow, West Vancouver, all of Canada

[73] Assignee: 410261 B.C. Ltd., West Vancouver, Canada

[21] Appl. No.: 851,878

[22] Filed: Mar. 16, 1992

[51] Int. Cl.$^5$ ............................................. C07C 2/00
[52] U.S. Cl. ................................ 585/500; 585/651; 585/652; 585/943
[58] Field of Search ............... 585/500, 656, 657, 658, 585/943; 502/344, 341

[56] References Cited

U.S. PATENT DOCUMENTS

| | | | |
|---|---|---|---|
| 3,586,733 | 6/1971 | Connor et al. | 585/658 |
| 4,073,875 | 2/1978 | Feilchenfeld | 423/636 |
| 4,499,322 | 2/1985 | Jones et al. | 585/500 |
| 4,517,398 | 5/1985 | Sofranko | 585/417 |
| 4,560,821 | 12/1985 | Jones et al. | 585/500 |
| 4,608,449 | 8/1986 | Baerns et al. | 585/500 |
| 4,658,074 | 4/1987 | Bajars et al. | 585/658 |
| 4,665,260 | 5/1987 | Jones et al. | 585/400 |
| 4,935,572 | 6/1990 | Erekson et al. | 585/415 |
| 4,952,743 | 8/1990 | Come | 585/541 |
| 5,053,578 | 10/1991 | Michaels et al. | 585/500 |
| 5,118,654 | 6/1992 | Choudhary et al. | 585/500 |
| 5,132,482 | 7/1992 | Smith et al. | 585/500 |

OTHER PUBLICATIONS

Sofranko et al, The Oxidative Conversion of Methane to Hydrocarbons, 1987 Journal of Catalysis pp. 302–310.
Keller et al, Synthesis of Ethylene via Oxidative Coupling of Methane, 1982, Journal of Catalysis pp. 9–19.
Lee et al, Oxidative Coupling of Methane to Higher Hydrocarbons, 1988, Catal. Rev.-Sci. Eng. pp. 249–279.
Bibby et al, Feasibility of Ethylene Synthesis via Oxidative Coupling of Methane, 1988, pp. 343–357.
Otsuka et al, Active and Selective Catalysts for the Synthesis of $C_2H_4$ via Oxydative Coupling of Methane, 1986, pp. 353–359.
Ito et al, Oxidative Dimerization of Methane over a Lithium-Promoted Magnesium Oxide Catalyst, 1985, J. Am. Chem. Soc., pp. 4808–4810.
Lin et al, Oxidative Dimerization of Methane over Magnesium and Calcium Oxide Catalysts Promoted with Group 1A Ions: The Role of [M+O$^o$] Centers, 1987, J. Am. Chem. Soc., pp. 5062–5068.
Cant et al, The Rate of Controlling Step in the Oxidative Coupling of Methane over a Lithium-Promoted Magnesium Oxide Catalyst, 1988, J. Chem. Soc., pp. 766–768.
Buevskaya et al, Activation of Hydrocarbons in the Oxidative Dimerization of Methane Over Alkaline Earth Metals, 1987, pp. 223–227.
Otsuka et al, Kinetic Studies on Partial Oxidation of Methane over Samarium Oxides, 1986, Inorganica Chimica Arta, pp. 237–241.
Emesh et al, Oxidative Coupling of Methane over the Oxides of Group IIIA, IVA, and VA Metals, 1986, J. Phys. Chem., pp. 4785–4789.
Jones et al, The Oxidative Conversion of Methane to Higher Hydrocarbons over Alkali-Promoted Mn/SiO$_2$, 1987, Journal of Catalysts, pp. 311–319.

*Primary Examiner*—Anthony McFarlane
*Attorney, Agent, or Firm*—Norman M. Cameron

[57] ABSTRACT

A catalyst having the composition A:Al$_2$O$_3$ is used as a catalyst for producing ethylene from methane. A is an alkali metal, preferably lithium. The catalyst may be doped with an additive such as MgCl$_2$. A weak oxidation catalyst such as MoO$_3$ or ZrO$_2$ may be added. The catalyst is heated to at least 750° C. in a catalytic reactor and a mixture of air and methane is passed over the heated catalyst. Oxygen or air may be added part way along the catalytic reaction to oxidize H$_2$ but not C$_2$H$_4$.

8 Claims, 10 Drawing Sheets

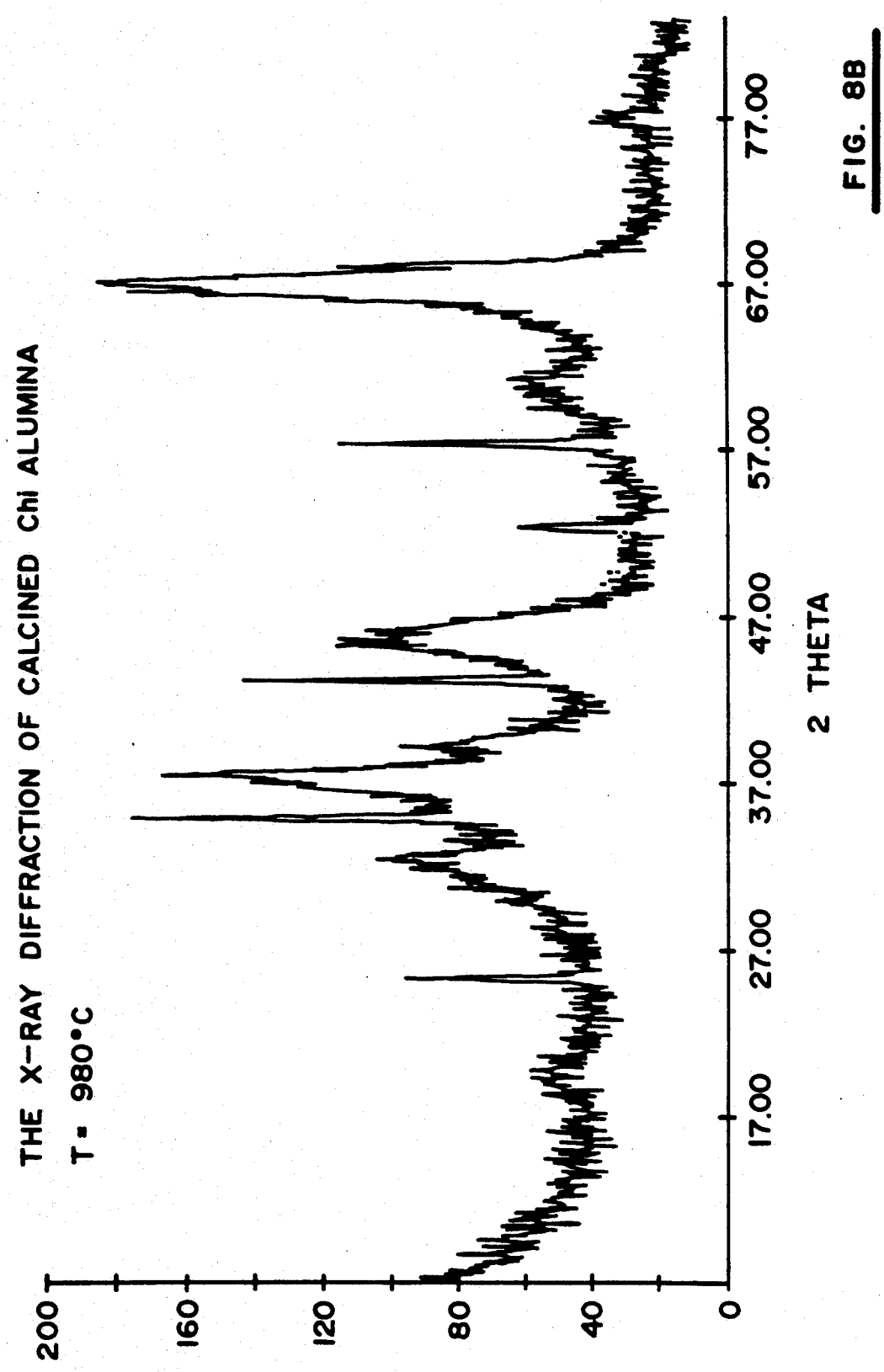

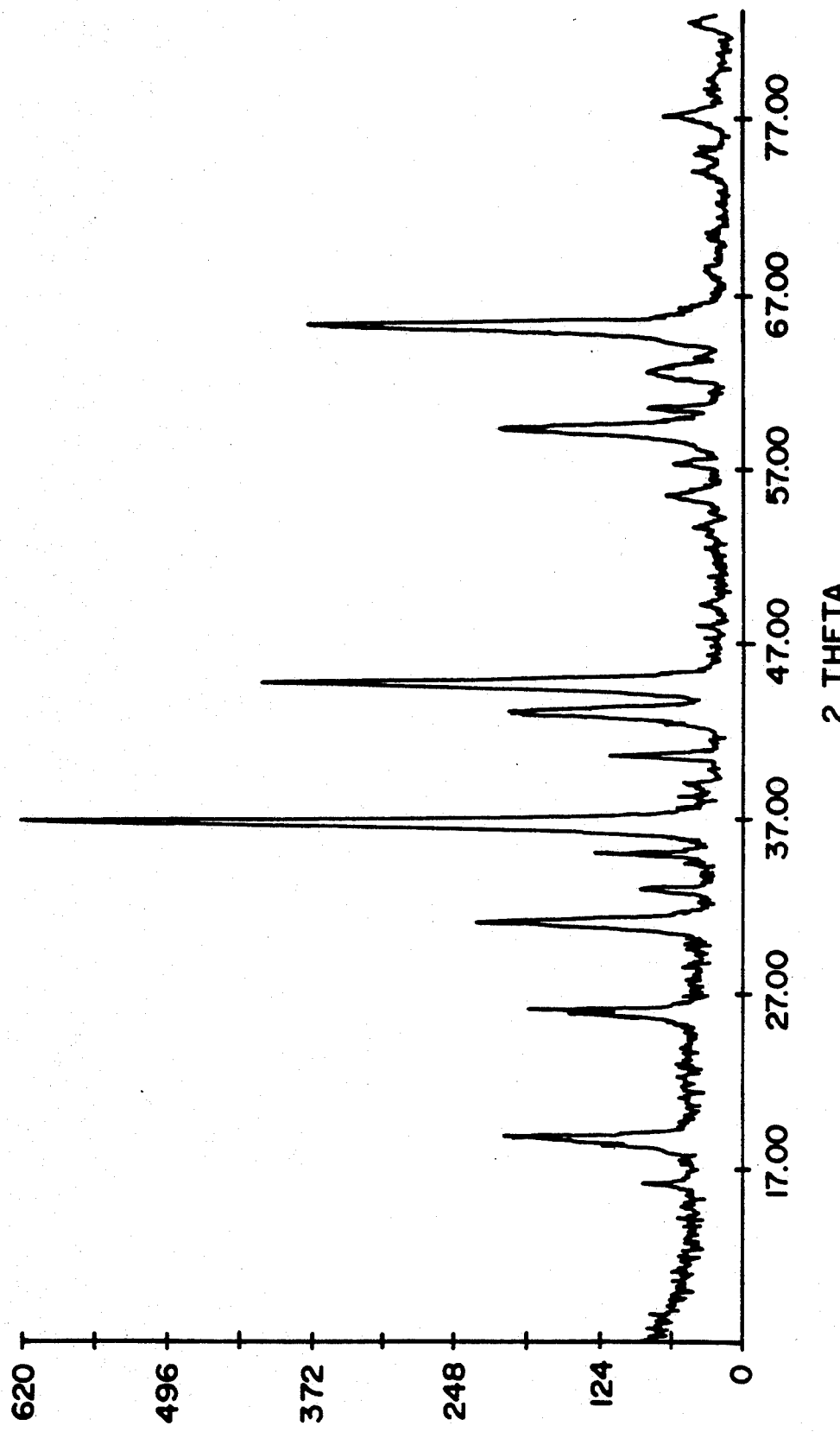

ETHYLENE FROM METHANE AND CATALYSTS THEREFOR

BACKGROUND OF THE INVENTION

1. Field of the Invention

This invention relates to the production of ethylene from methane and to catalysts used therefor.

2. Description of Related Art

Methane is a naturally occurring substance and is the main constituent in natural gas. It is presently an abundant resource available at a modest cost.

Ethylene is a gas which is one of the basic building blocks of the petrochemical industry for making such products as polyethylene. Accordingly, considerable research has been directed toward converting low cost methane to ethylene. Conventionally the methane is reacted with oxygen to form ethylene and water. The objects of the research are a high selectivity to ethylene, and perhaps other hydrocarbons, a high conversion per pass of $CH_4$, and a high throughput overall.

Much of the research has focused on finding the best catalyst for the reaction. Many oxides have been tested. All are most active at about 1000 K. Some of the best reported combinations are $Sm_2O_3$, $CeO_2/1\%$ Ba, BeO/1% Li, $La_2O_3/1\%$ Sr, $Al_2O_3/20\%$ Pb, and $LaAlO_2$.

Two of the best catalysts found have been $SrCe_{0.9}Yb_{0.1}O_{2.95}$ and $MnO_2/20\%$ LiCl. However, for both of these catalysts, the space time yield ($\mu$ moles/sec g) is very low, suggesting that the flow rate must be kept very low. These catalysts are discussed in an article by G. J. Hutchings, M. S. Scurrell and J. R. Woodhouse, Chem. Soc. Rev. 18, 251 (1989).

According to Y. A. Amenomiya, V. I. Birss, M. Goledzinowski, J. Galuazka and A. R. Sanger, in "Conversion of Methane by Oxidative Coupling", report to CANMET, Energy, Mines and Resources, Ottawa, Canada, the various promising catalysts are rated in order as $Li/Sm_2O_3 > Na/CaO > K/CaO > LaAl_2O_3 > Sm_2O_3 > Li/CaO > PbO > Bi_2O_3 > Ho_2O_3 > Gd_2O_3 > Li/MgO > Li/CaO \sim Yb_2O_3 > Y_2O_3 Na/MgO \sim CaO > MgO$. Additives to the catalysts include Ba, Li, Sr, Pb, K, Mg, Ca, Na, and Sb.

Many other catalysts have been tested for methane oxidative coupling including lithium deposited on $\alpha Al_2O_3$. However, the conversion rate was found to be low. The consensus in the literature has been that an acid catalyst must be poor, and because $Al_2O_3$ is highly acid, there has been little interest in this possibility.

In short, while many catalysts have been explored for converting methane to ethylene, all of those tested have fallen short of the goals of high selectivity to ethylene, a high conversion per pass of $CH_4$, and a high throughput overall.

SUMMARY OF THE INVENTION

It is therefore and object of the invention to provide an improved catalyst for converting methane to ethylene.

It is also an object of the invention to provide an improved process for the conversion of methane into ethylene.

It is a further objection of the invention to provide an improved apparatus for converting methane to ethylene.

In accordance with these objects, a first aspect of the invention provides a process for producing ethylene which comprises combining air and methane in the presence of an oxidative coupling catalyst having the composition $A:Al_2O_3$, where A is an alkali metal. Preferably the air and methane are combined in the presence of a weak oxidative catalyst which oxidizes $H_2$, but not $C_2H_4$ at 750° C., such as $MoO_3$ or $ZrO_2$.

A second aspect of the invention provides a process for producing methane, comprising passing a mixture of $O_2$ and methane over a heated catalyst, introducing additional $O_2$ to oxidize the $H_2$ produced and passing the mixture over more heated catalyst.

A third aspect of the invention provides an apparatus for producing methane, comprising one or more catalytic reactors having first inlet means for admitting a mixture of $O_2$ and methane into the one or more reactors, an outlet for ethylene and second inlet means between the first inlet means and the outlet to admit $O_2$ to oxidize $H_2$ produced in the one or more reactors.

A fourth aspect of the invention provides a method for producing a catalyst for converting methane to ethylene. The method comprises adding a solution of an alkali metal hydroxide to alumina. The alumina may be calcined at a temperature of 980° C. before adding the alkali metal hydroxide solution. The catalyst may be sintered at a temperature of 850° C. to 900° C., preferably 850° C., after treatment with the hydroxide. The catalyst may be doped with a metallic salt, such as $MgCl_2$ before the calcining.

A fifth aspect of the invention provides a catalytic composition comprising a powdered mixture of $A:Al_2O_3$, where A is an alkali metal, and a compound selected from the group consisting of $MoO_3$ and $ZrO_2$.

A sixth aspect of the invention provides a catalytic composition having the formula $A:Al_2O_3$, where A is an alkali metal prepared by impregnating porous $Al_2O_3$ with an alkali metal hydroxide, then sintering at a temperature near 850°–900° C., preferably 880° C.

BRIEF DESCRIPTION OF THE DRAWINGS

In the drawings:

FIG. 8b is the x-ray diffraction pattern of the alumina after calcining; and

FIG. 8c is the x-ray diffraction pattern of the catalyst without promoter after heat treatment at 880° C.

DESCRIPTION OF THE PREFERRED EMBODIMENTS

1. The Catalyst

The preferred main coupling catalyst is lithium aluminate+Mg (as $MgCl_2$) sintered at a temperature of 880° C. Other additives besides Mg have been tested such as Sm, Pb, Ce and Mn, but none are as effective as Mg although they could be used. In addition, other alkali metals can replace Li. K and Na are moderately effective, but the selectivity is significantly less than for Li. Rb and Cs may also work, but it is believed that the catalyst is less active for larger alkali atoms.

The catalyst is in powder form and includes a second catalytic component in the preferred embodiment to prevent the back reaction of $C_2H_4$ to $CH_4$. $MoO_3$ and $ZrO_2$ will oxidize $H_2$ but not $C_2H_4$ as is desired. Other catalysts undoubtedly will be found that catalyze the oxidation of $H_2$ but not $C_2H_4$ at about 750° C. A material with these characteristics will greatly enhance the $CH_4 \rightarrow C_2H_4$ reaction. Those oxides found to be unsuitable include $TiO_2$, $ZnO$, $Fe_2O_3$, $Mn_2O_3$ and $Cr_2O_3$, because they are too active at 775° C. in oxidizing $C_2H_4$.

2. Process for Making the Catalyst

As stated above, $Al_2O_3$ was overlooked as a potential catalyst for producing ethylene from methane because it is highly acid. In the preparation procedure according to the invention, it is believed that all the acid sites have been neutralized by a novel high temperature lithium treatment. In brief, a key step in producing the coupling catalyst has been the addition of LiOH to porous alumina followed by calcining at an extremely high temperature, 850° C. to 900° C. and preferably 880° C., to induce the Li to dissolve into the bulk $Al_2O_3$ to form a lithium aluminate (as opposed to an alumina with LiOH simply deposited on its surface). The catalyst is impregnated with $MgCl_2$, usually before the calcining step.

EXAMPLE 1

Figure 8A:
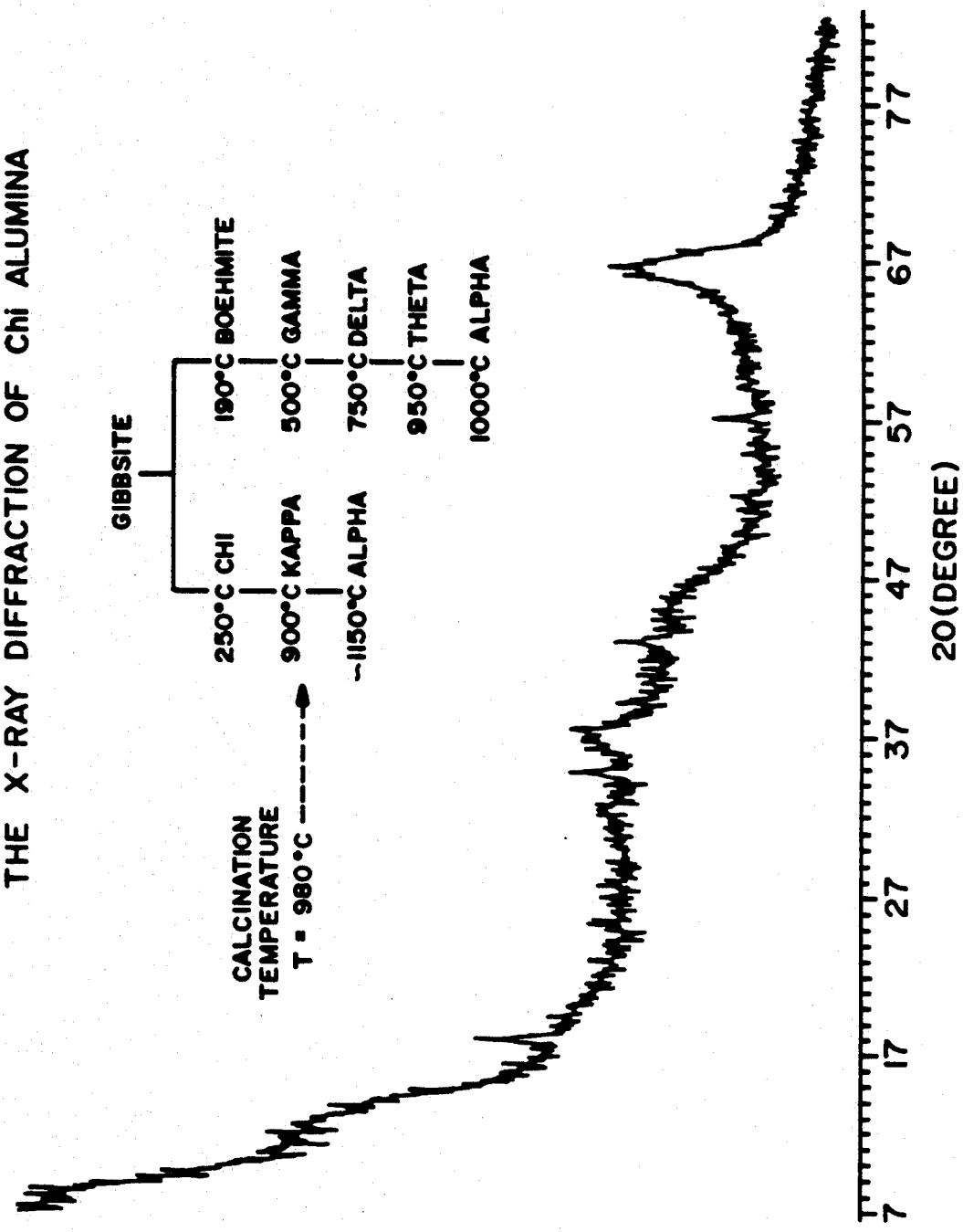
FIG. 8a is the x-ray diffraction pattern of the as-received alumina.

The basic coupling catalyst was produced by calcining about 1 gram of Alcan AA-101 Chi (Trademark) alumina, a porous $Al_2O_3$ powder of 5-25 microns in particle diameter. The specified alumina is obtained by temperature treatment of parent gibbsite at 250° C. The alumina is calcined at 980° C. for a minimum of five hours in flowing air and then quenched to room temperature. FIG. 8a is the x-ray diffraction pattern of the as-received alumina, while FIG. 8b is the x-ray diffusion pattern after the calcining at 980° C.

The heat treated alumina powder was slurried with 15 cc of 0.2M LiOH and dried at 100° C. with continuous stirring. The basic catalyst thus produced was mixed with 8 cc of 0.2M $MgCL_2$ into a slurry and slowly dried at 100° C. with continuous stirring.

The powder mixture was then ground to fine size particles and sintered in air at 880° C. for another five hours and quenched to room temperature. FIG. 8c shows the x-ray diffusion pattern of the catalyst after the heat treatment. If the sintering step is omitted, the catalyst's conversion rate is poor and slow at the beginning, but recovers to its optimum activity over an operating time of 30 hours approximately. The catalyst so prepared was further ground to fine powder before being packed in the reactors.

EXAMPLE 2

The Mg doped coupling catalyst prepared above was promoted by mixing the catalyst powder with as received $MoO_3$ powder in equal weight and ground to ensure an even mixture, with maximum distribution of the $MoO_3$ particles in the catalyst powder. The analysis of the mixture showed an Al/Mo atomic ratio of 5.4 for the best performance. The ratio of coupling catalyst to $MoO_3$ depends somewhat on the flow rate of methane used. A higher flow rate requires more $MoO_3$ to effectively remove (by oxidation) the $H_2$. Too much $MoO_3$ initiates some undesirable oxidation of the carbon containing gases.

3. Apparatus for Producing Ethylene

Figure 1:
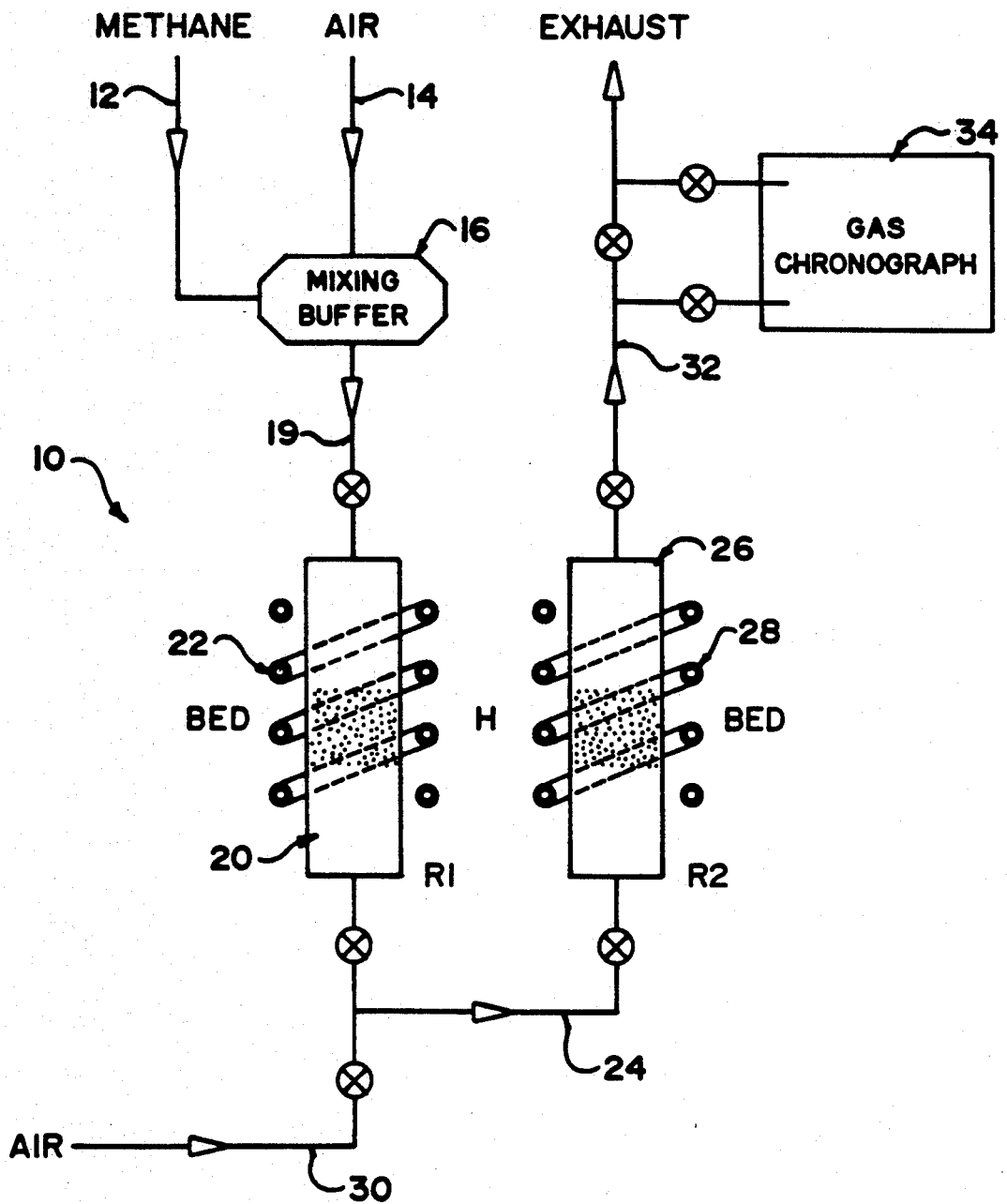
FIG. 1 is a schematic drawing of an apparatus and process for producing ethylene from methane according to an embodiment of the invention.

Referring to FIG. 1, this shows an apparatus 10, according to an embodiment of the invention, for producing ethylene from methane. It includes an inlet conduit 12 for methane, an inlet conduit 14 for air, both of which are connected to a buffer 16 for mixing the air and methane. A conduit 18 connects the mixing chamber with a first reactor 20. The reactor is made of quartz tubing of 1.076 cm inside diameter in this example. A heater 22 extends about the reactor. A conduit 24 connects the first reactor to a second and similar reactor 26 which is similarly provided with a heater 28. An air inlet conduit 30 is connected to conduit 24 to admit air, and consequently oxygen, into the mixture after the first reactor. There is an exhaust conduit 32 connected to the second reactor for the discharge of ethylene from the apparatus 10. A Gas Chromatograph 34 was employed for analyzing the reaction components.

Additional reactors or beds could be used besides the two illustrated. Alternatively, a single bed could be possible with the additional air being added part way through the single reactor instead of being between two separate reactors as illustrated.

4. Process for Producing Ethylene

In the experiment, 100 mg of powder catalyst produced by the process above was distributed over quartz wool in each of the reactors 20 and 26 shown in FIG. 1. The heaters 22 and 28 were used to independently increase the temperature of the catalyst to 775° C. Air and methane were introduced at one atmosphere pressure as a $O_2/CH_4=1.5$ mixture. The flow rates of methane and air were increased, maintaining the same ratio. Heat from the reaction caused an uncontrolled increase in the catalyst's temperature to about 800° C. In the case of the two-bed reactor shown, another flow of air was provided through conduit 30 and the added flow was optimized at 20 ml/min., to maintain the best yield.

Figure 6:
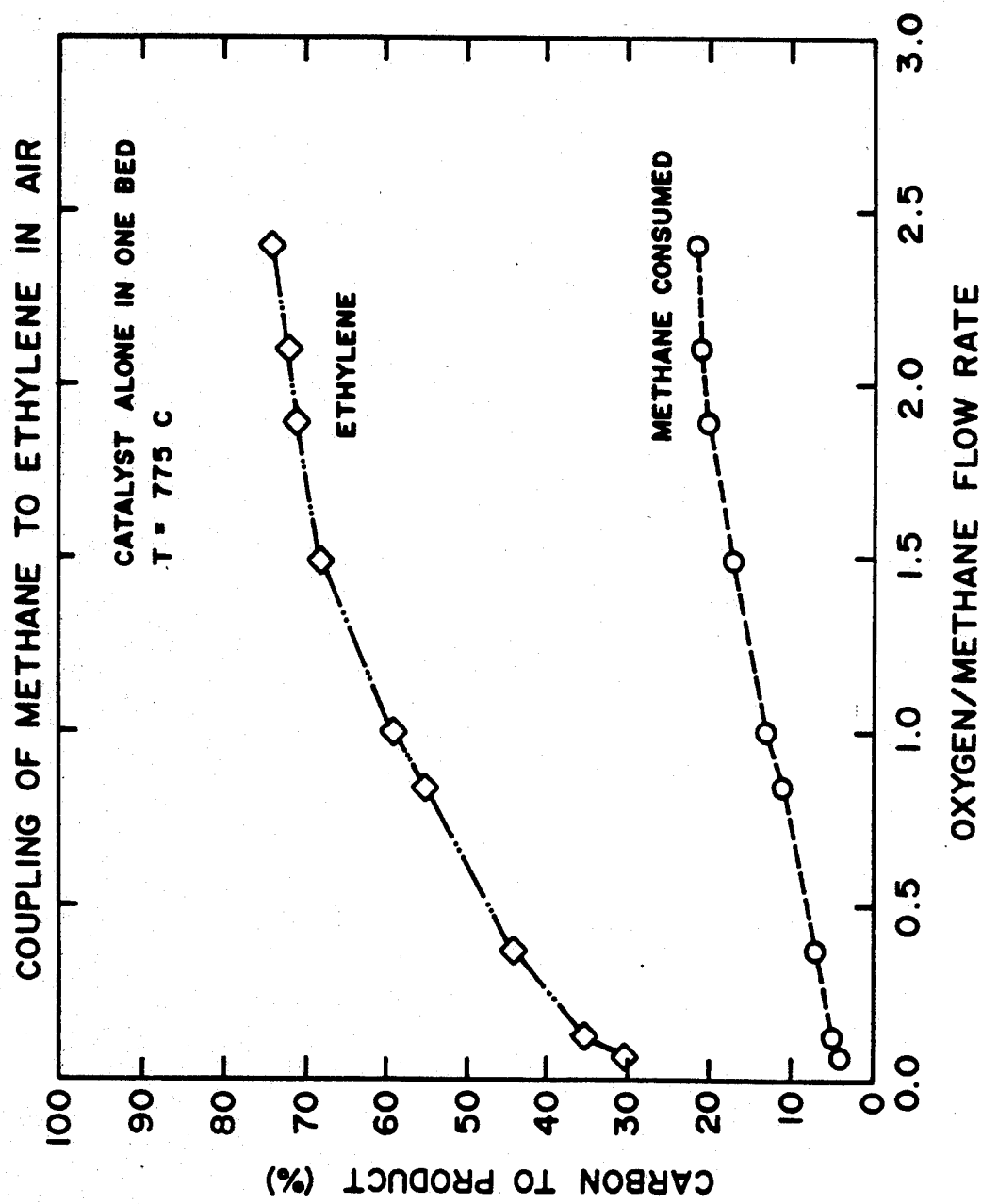
FIG. 6 is a graph showing the conversion of methane and the percentage of carbon going to ethylene plotted against the oxygen/methane flow ratios for catalyst without the promoter in a one bed reactor.
Figure 7:
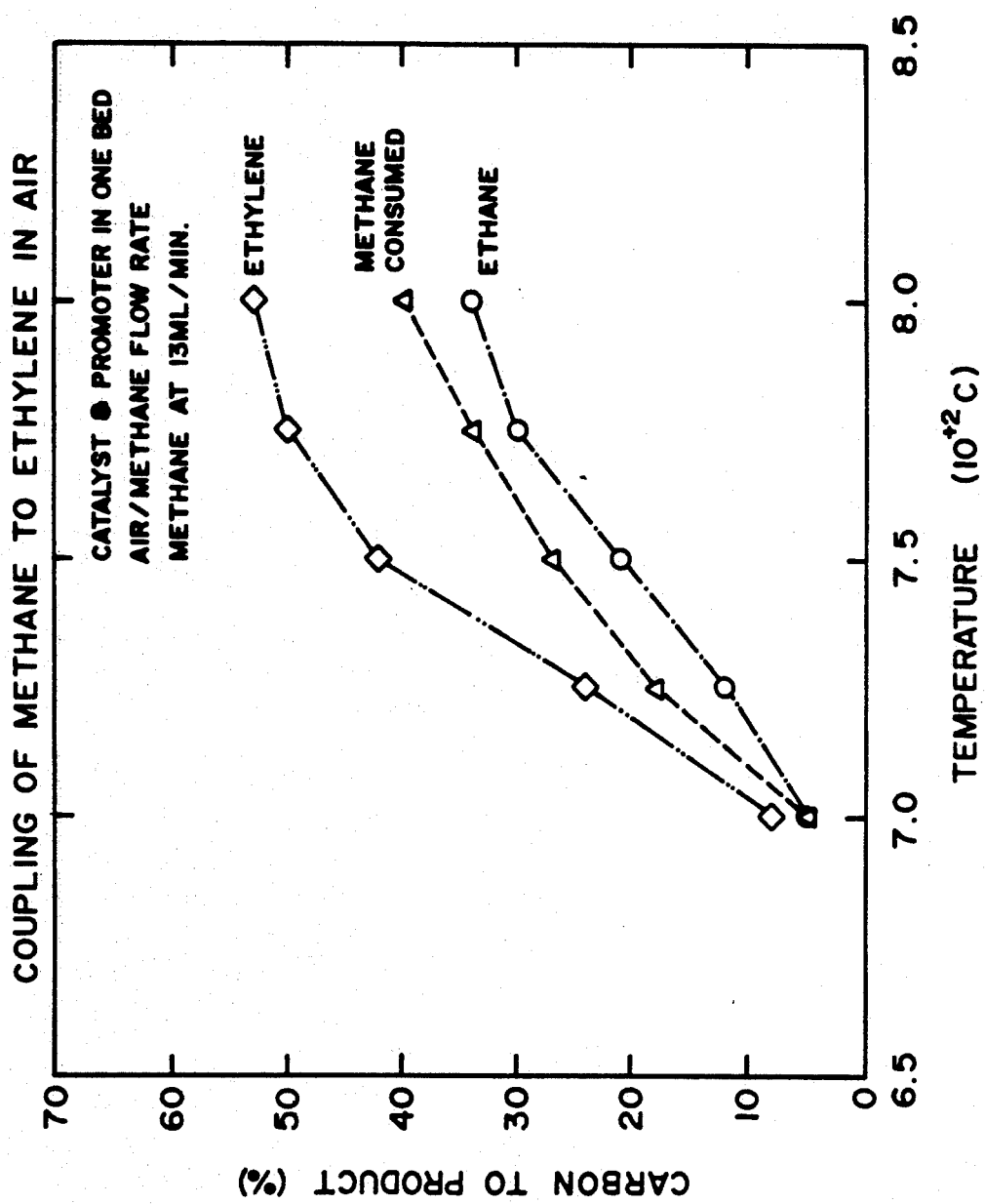
FIG. 7 is a graph showing the percentage of methane consumed and the percentages of products produced for different temperatures of reaction.

FIG. 6 shows the percentage of methane converted and the percentage of carbon going to ethylene plotted against the oxygen/methane flow ratios for the catalyst alone in a one-bed reactor.

Figure 2:
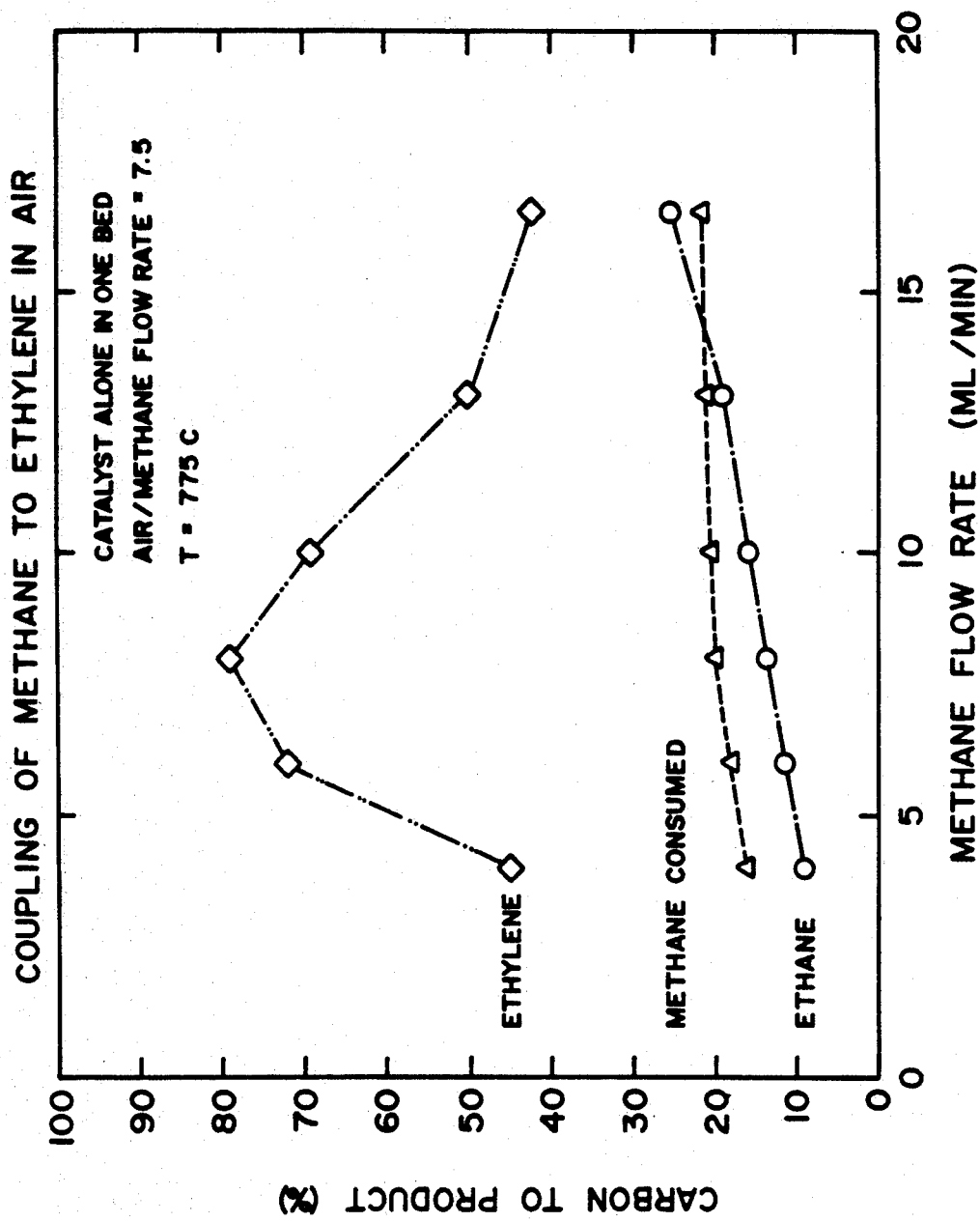
FIG. 2 is a graph showing the conversion of $CH_4$, and the percentage of carbon going to $C_2H_4$ and other products plotted against the flow rate of methane.

Referring to FIG. 2, the lithium aluminate/Mg catalyst by itself converts methane effectively to ethylene in the oxidative coupling reaction, but only at a relatively low flow rate. A high selectivity of up to 80% is achieved, but only at a modest flow rate of about 7 ml/min. in this example. To the left of the peak the gas has too long a contact time on the catalyst. Following or during the desired reaction

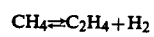
$$CH_4 \rightleftharpoons C_2H_4 + H_2$$

the hydrogen and much of the $C_2H_4$ is oxidized because they contact the catalyst too long in the presence of oxygen. The peak occurs when the contact time is long enough to oxidize the hydrogen but not the ethylene. At higher flow rates the hydrogen generated by the above reaction is not consumed and the hydrogen blocks the desired reaction, either by poisoning sites or by inducing the reverse reaction of the above reaction, limiting the $C_2H_4$ produced, or both.

Figure 3:
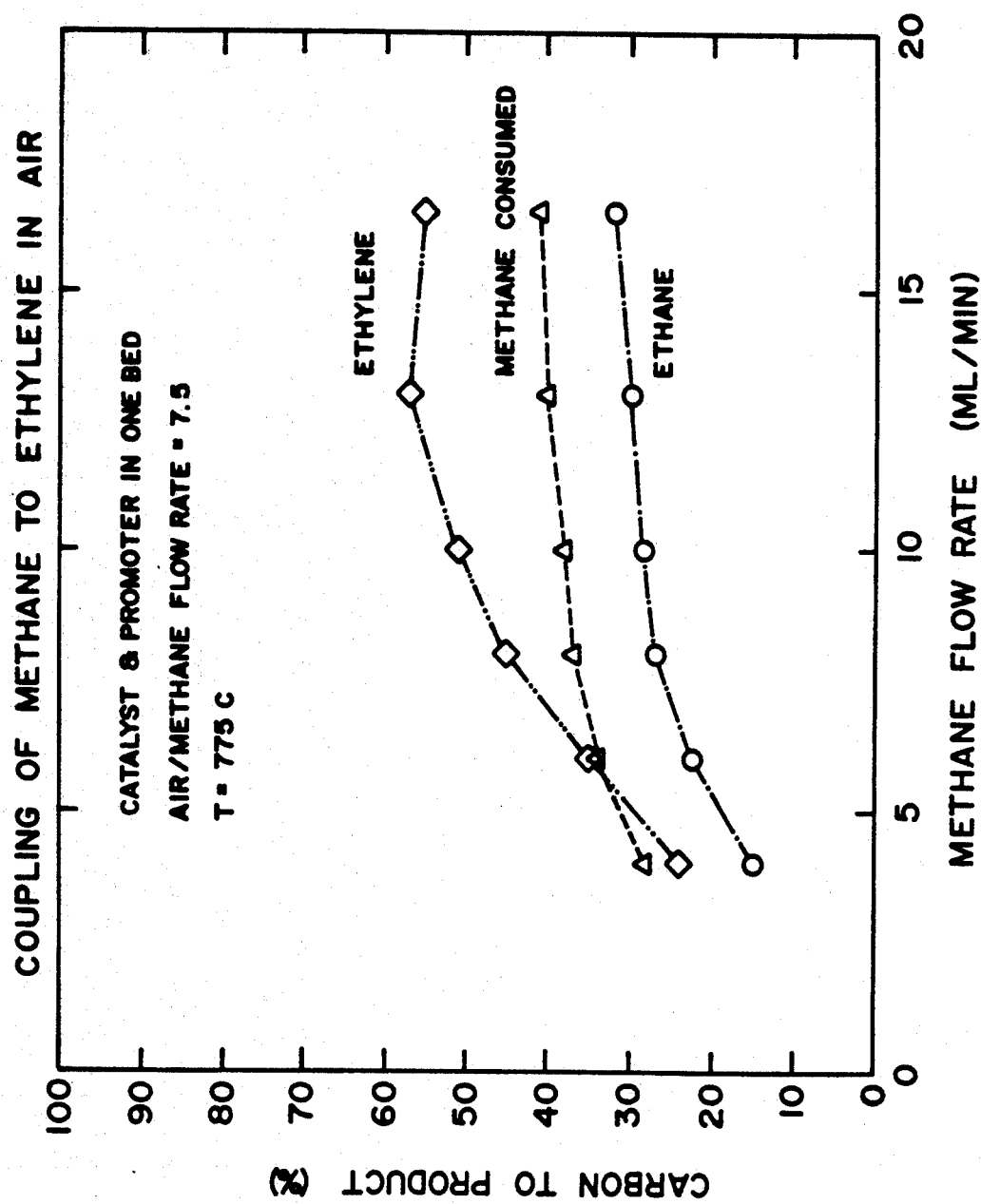
FIG. 3 is a graph similar to FIG. 2, but in this case the promoter $MoO_3$ is mixed with the $Li:Al_2O_3$ catalyst.
Figure 4:
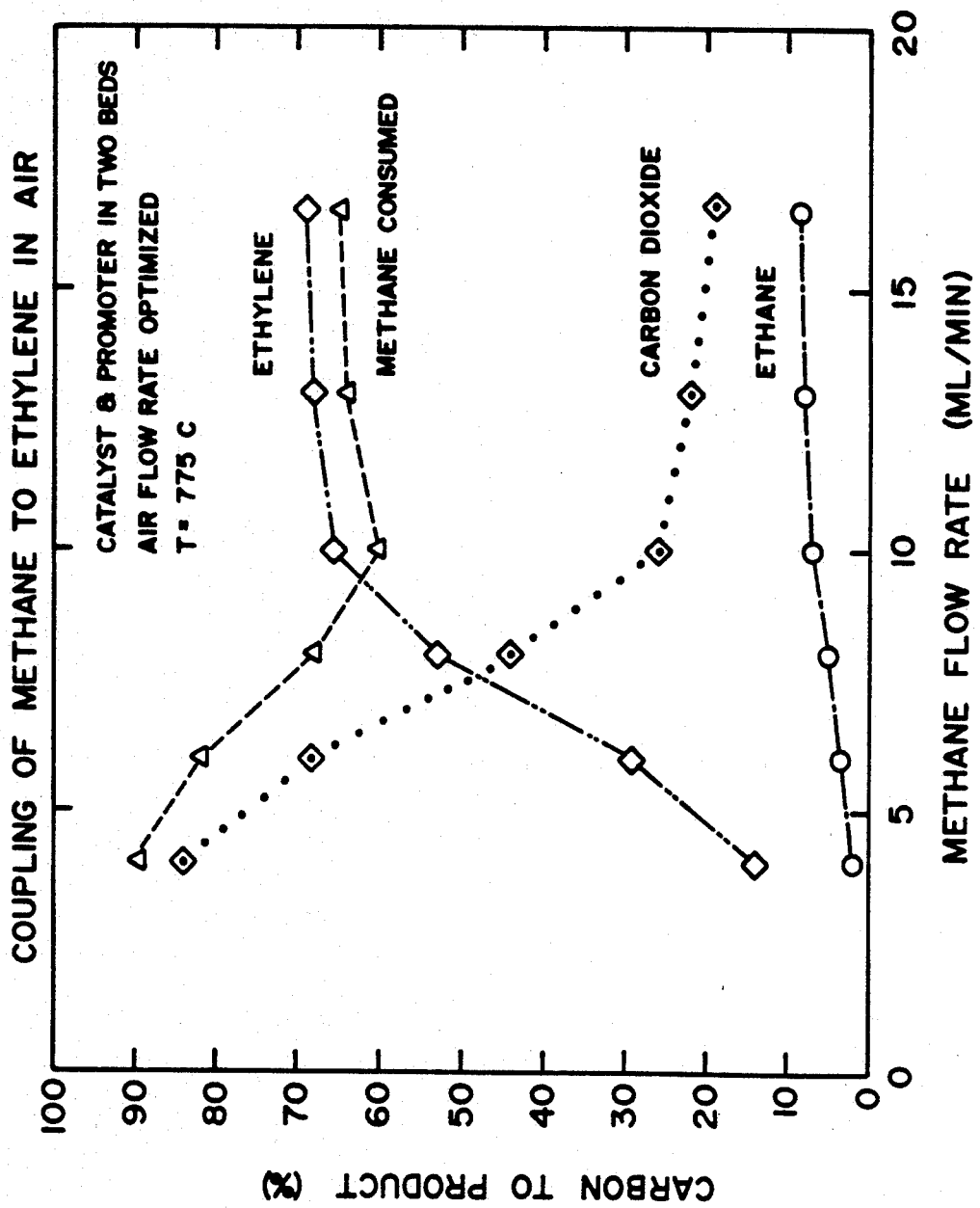
FIG. 4 is a graph similar to FIG. 2, showing the results where the oxygen supply is refreshed part way through the catalyst system.
Figure 5:
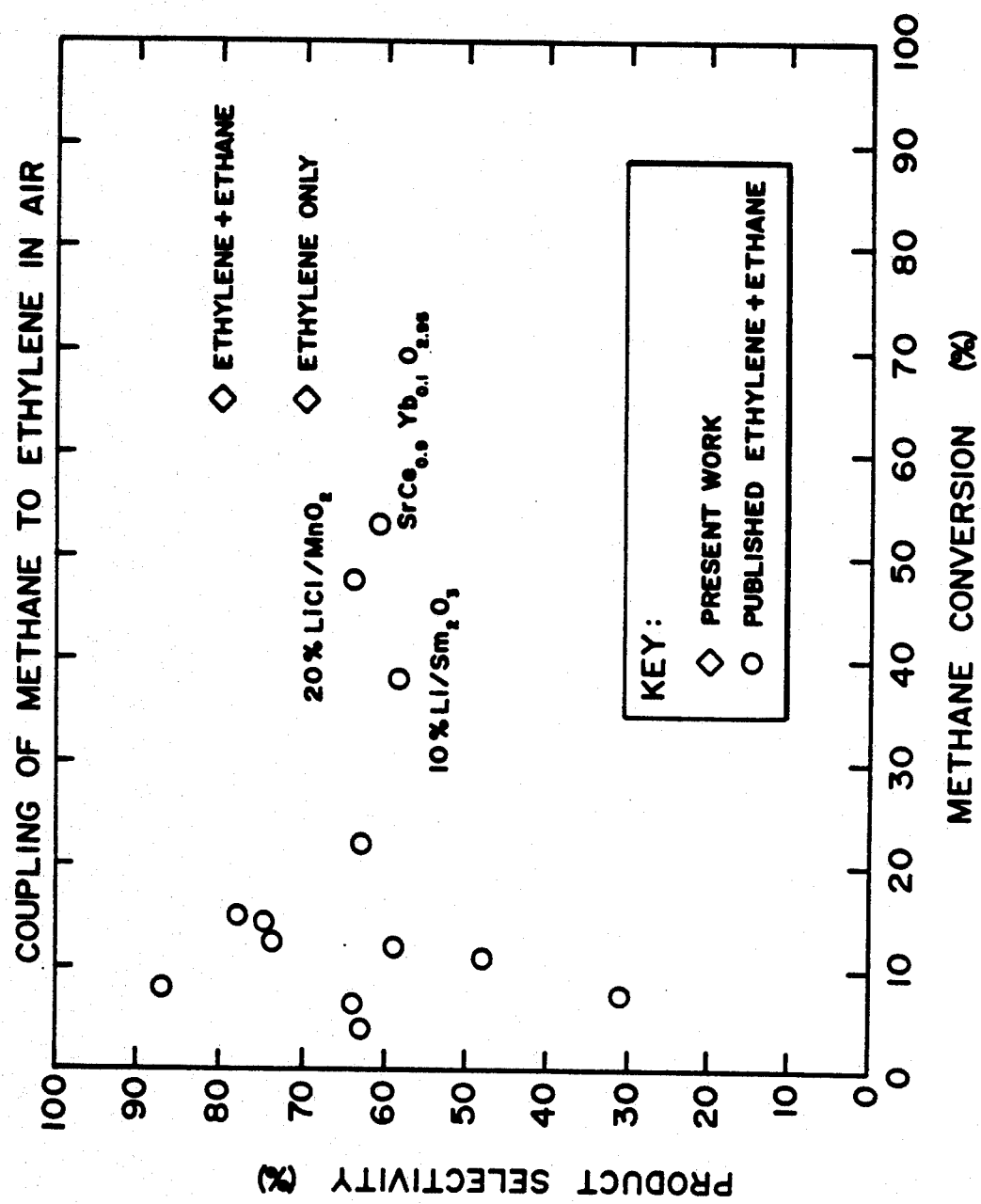
FIG. 5 is a graph showing the specificity of the conversion of $CH_4$ to $C_2H_4$ and $C_2H_6$ plotted against the percentage of methane converted and showing a comparison of the invention with prior art.

With this in mind, a co-catalyst was sought to catalyze the oxidation of $H_2$ ($H_2 + \frac{1}{2}O_2 \rightarrow H_2O$), but not the oxidation of $C_2H_4$ ($C_2H_4 + 3O_2 \rightarrow 2CO_2 + 2H_2O$). The preferred co-catalyst, which is termed "promoter", is $MoO_3$. Referring to FIG. 3, with the promoter, the selectivity is weakened compared to FIG. 2, but the $CH_4$ conversion is much higher and the flow rate can be much higher, increasing the rate of ethylene formed, in other words the throughput. The novelty is the realization that removing the hydrogen selectively improves the reaction characteristics and the identification of catalysts that perform this function. The oxidation of the hydrogen produced, in principle to prevent the back reaction of the $C_2H_4$ to $CH_4$, increased the methane conversion by a factor of more than 2, as shown in FIG. 3.

The optimum temperature of the reaction is about 775° C. However, a range of 775° C. to 800° C. is satisfactory, as seen in FIG. 2, although temperatures of 700° C. to 750° C. work to some extent.

It was also discovered that the oxygen should be "bled in". In other words, when the reaction

$$CH_4 + O_2 \rightarrow C_2H_4 + H_2O$$

proceeds as desired, one cannot mix all the oxygen required with the $CH_4$ immediately because with too much oxygen $CO_2$ forms. To avoid excess $CO_2$, part of the oxygen needed for consumption of the hydrogen is introduced initially, then, when it is consumed, the rest of the oxygen is introduced to complete the reaction. This makes a high flow rate possible while maintaining a high conversion selectivity.

The concept of introducing air at various points along the catalyst bed so the oxygen content is not too high (forming $CO_2$) or too low (not providing the sites to break up $CH_4$ or the oxygen needed to oxidize $H_2$) is also novel. Those skilled in the art will recognize that a more elaborate reactor, where oxygen (air) is admitted at many points along the catalyst bed to provide exactly the right pressure at each point will undoubtedly improve the selectivity further.

At its present stage of development, in one pass the catalyst converts 65% of methane passing over it with 70% of the carbon converted to ethylene and 10% to ethane, with the remaining 20% lost as $CO_2$. There is no obvious limit on the throughput of the system disclosed.

It will also be recognized by someone skilled in the art that many of the details provided above are by way of example only and are not intended to limit the scope of the invention which is to be interpreted with reference to the following claims.

What is claimed is:

1. A process for producing ethylene comprising: combining air and methane in the presence of an oxidative coupling catalyst, the catalyst being lithium aluminate.

2. A process as claimed in claim 1, wherein the air and methane are reacted at a temperature of 775° C. to 800° C.

3. A process as claimed in claim 1, wherein the air and methane are reacted at a temperature of 775° C.

4. A process as claimed in claim 1, wherein the catalyst is doped with an additive selected from the group consisting of salts of Mg, Sm, Pb, Ce and Mn.

5. A process as claimed in claim 4, wherein the additive is $MgCl_2$.

6. A process as claimed in claim 1, wherein the air and methane are combined in the presence of a weak oxidation catalyst which oxidizes $H_2$, but not $C_2H_4$ at 750° C.

7. A process as claimed in claim 6, wherein the weak oxidation catalyst is selected from the group consisting of $MoO_3$ and $ZrO_2$.

8. A process as claimed in claim 1, wherein the oxidative coupling catalyst is in a bed and $O_2$ is introduced along the bed at a plurality of points so the $O_2$ is high enough to oxidize excess $H_2$, but not high enough to form $CO_2$.

* * * * *